US009448216B2

(12) United States Patent
Jin et al.

(10) Patent No.: US 9,448,216 B2
(45) Date of Patent: Sep. 20, 2016

(54) GAS SENSOR DEVICE WITH FRAME PASSAGEWAYS AND RELATED METHODS

(71) Applicant: STMICROELECTRONICS PTE LTD, Singapore (SG)

(72) Inventors: Yonggang Jin, Singapore (SG); Ravi Shankar, Singapore (SG)

(73) Assignee: STMICROELECTRONICS PTE LTD, Singapore (SG)

( * ) Notice: Subject to any disclaimer, the term of this patent is extended or adjusted under 35 U.S.C. 154(b) by 0 days.

(21) Appl. No.: 14/511,280

(22) Filed: Oct. 10, 2014

(65) Prior Publication Data

US 2016/0103109 A1 Apr. 14, 2016

(51) Int. Cl.
*G01N 27/12* (2006.01)
*G01N 33/00* (2006.01)

(52) U.S. Cl.
CPC .................................. *G01N 33/0009* (2013.01)

(58) Field of Classification Search
None
See application file for complete search history.

(56) References Cited

U.S. PATENT DOCUMENTS

| 2009/0020862 | A1* | 1/2009 | Chen | B81B 7/0061 257/676 |
| 2011/0165719 | A1* | 7/2011 | Solzbacher | G01L 9/0042 438/53 |
| 2011/0233739 | A1* | 9/2011 | Wakisaka | B81B 7/007 257/666 |
| 2013/0008787 | A1* | 1/2013 | Mammoto | G08B 17/10 204/407 |
| 2013/0043575 | A1* | 2/2013 | Theuss | H01L 23/3107 257/676 |
| 2013/0126947 | A1* | 5/2013 | Wilbertz | H01L 29/66 257/253 |
| 2014/0070337 | A1* | 3/2014 | Besling | H01L 21/77 257/415 |
| 2015/0177171 | A1* | 6/2015 | Kim | G01N 27/128 73/31.05 |

* cited by examiner

*Primary Examiner* — Michael Lebentritt
*Assistant Examiner* — Jordan Klein
(74) *Attorney, Agent, or Firm* — Allen, Dyer, Doppelt, Milbrath & Gilchrist, P.A.

(57) ABSTRACT

A gas sensor device may include a gas sensor integrated circuit (IC) having a gas sensing surface, and bond pads adjacent to the gas sensing surface, and a frame having gas passageways extending therethrough adjacent the gas sensing surface. The gas sensor device may include leads, each having a proximal end spaced from the frame and bonded to a respective bond pad, and a distal end extending downwardly from the proximal end, and encapsulation material filling the space between the proximal ends of the leads and the frame.

23 Claims, 5 Drawing Sheets

GAS SENSOR DEVICE WITH FRAME PASSAGEWAYS AND RELATED METHODS

TECHNICAL FIELD

The present disclosure relates to the field of integrated circuit devices, and, more particularly, to gas sensor integrated circuit devices and related methods.

BACKGROUND

Gas sensor devices are used in many applications and may detect the presence of various gases in a certain area. For example, these gas sensor devices may be used to detect combustible, flammable, and toxic gases. Gas sensor devices may be used in larger safety alert systems (e.g. fire detection systems), generating an alarm when a gas is detected, or in control systems, selectively adjusting operational parameters when a gas is detected.

Referring initially to FIG. 1, an approach to a gas sensor device 90 is described. The gas sensor device 90 includes a substrate 91, and electrically conductive traces 92 on the substrate. The gas sensor device 90 includes a gas sensor integrated circuit (IC) 94 on the substrate 91, a bond wire 93 coupled between the electrically conductive traces 92 and the gas sensor IC, and a wire mesh 95 over the gas sensor IC and having a plurality of openings 96a-96c therein.

SUMMARY

Generally speaking, a gas sensor device may include a gas sensor IC having a gas sensing surface, and a plurality of bond pads adjacent thereto. The gas sensor device may also include a frame having a plurality of gas passageways extending therethrough adjacent the gas sensing surface, and a plurality of leads. Each lead may have a proximal end spaced from the frame and bonded to a respective bond pad, and a distal end extending downwardly from the proximal end. The gas sensor device may include encapsulation material filling the space between the proximal ends of the plurality of leads and the frame.

In particular, the frame, the encapsulation material, and the proximal ends of the plurality of leads may be aligned to define an upper surface of the gas sensor device. The frame and the gas sensing surface may be in spaced relation to define a gas sensing cavity therebetween. The gas sensor IC may have a backside surface opposite the gas sensing surface, and the distal ends of the plurality of leads may extend past the backside surface to define a recess.

In some embodiments, the gas sensor device may further include an adhesive layer between the gas sensor IC and the plurality of leads. Also, the gas sensor device may further comprise additional encapsulation material adjacent the plurality of leads to define a sidewall of the gas sensor device. Also, the frame may be rectangle-shaped, and each gas passageway may be cylinder-shaped. For example, the plurality of leads and the plurality of bond pads may each comprise at least one of copper and aluminum, and the encapsulation material may comprise a dielectric material.

Another aspect is directed to a method of making a gas sensor device. The method may include forming a frame having a plurality of gas passageways extending therethrough, and forming a plurality of leads, each having a proximal end spaced from the frame, and a distal end extending downwardly from the proximal end. The method may include positioning a gas sensor IC having a gas sensing surface adjacent the plurality of gas passageways, and a plurality of bond pads adjacent thereto and bonded to a respective proximal end. The method may further include forming encapsulation material filling the space between the proximal ends of the plurality of leads and the frame.

DETAILED DESCRIPTION

The present disclosure will now be described more fully hereinafter with reference to the accompanying drawings, in which several embodiments of the present disclosure are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout.

Figure 1:
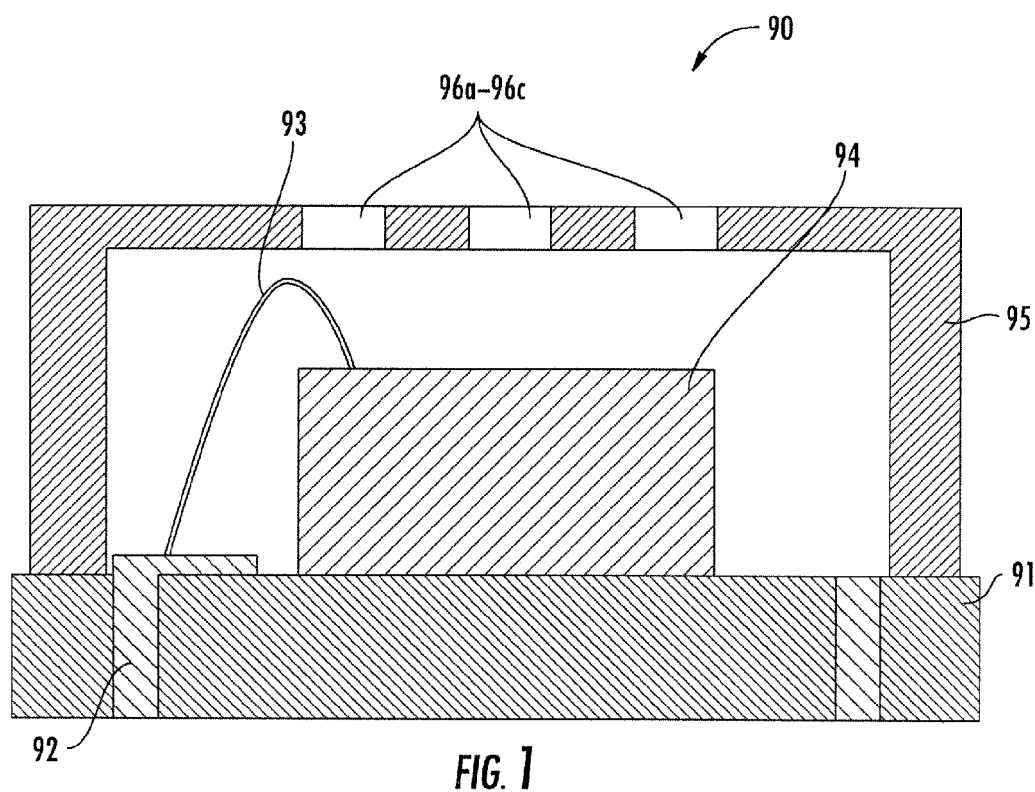
FIG. 1 is a schematic diagram of a cross-section view of a gas sensor device, according to the prior art.
Figure 2A:
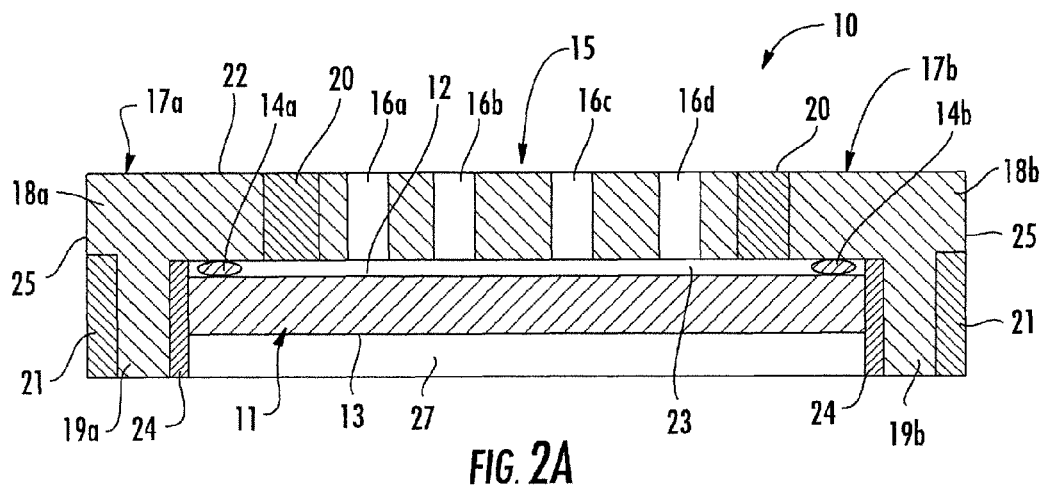
FIG. 2A is a schematic diagram of a cross-section view of a gas sensor device along line A-A, according to the present disclosure.
Figure 2B:
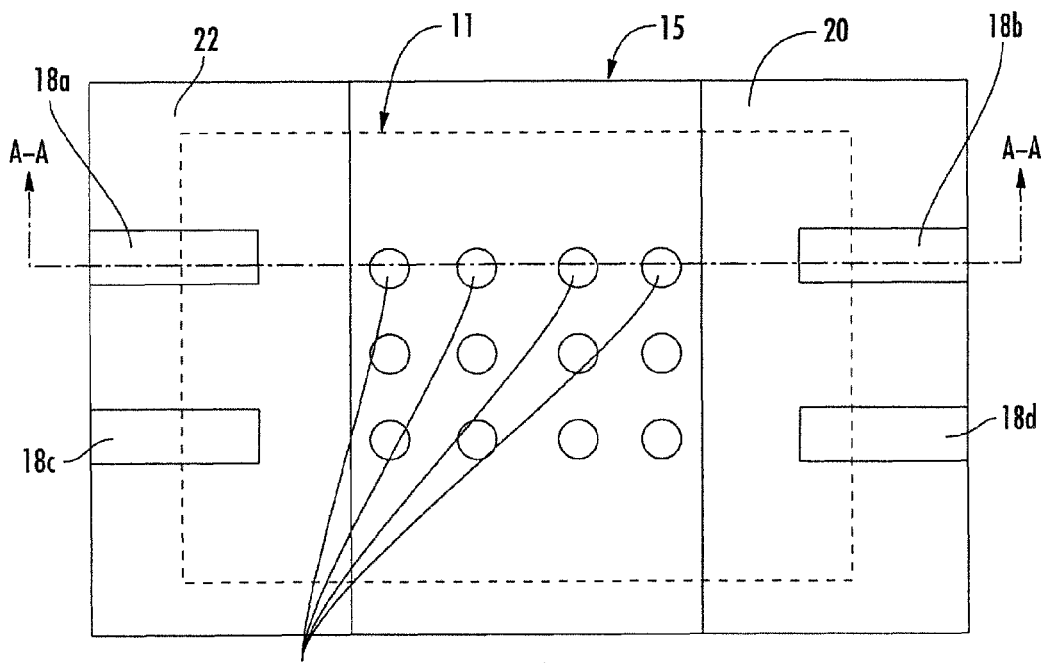
FIG. 2B is a schematic diagram of a top plan view of the gas sensor device of FIG. 2A.

Referring initially to FIGS. 2A-2B, a gas sensor device 10 according to the present disclosure is now described. The gas sensor device 10 illustratively includes a gas sensor IC 11 having a gas sensing surface 12, a plurality of bond pads 14a-14b adjacent thereto, and a backside surface 13 opposite the gas sensing surface. The gas sensor device 10 illustratively includes a frame 15 having a plurality of gas passageways 16a-16d extending therethrough adjacent the gas sensing surface 12. The plurality of gas passageways 16a-16d may each have a diameter from 0.25 mm to 0.8 mm, with a space between the passageways being from 0.25 mm to 0.5 mm.

The gas sensor device 10 illustratively includes a plurality of leads 17a-17b. Each lead 17a-17b illustratively includes a proximal end 18a-18b spaced from the frame 15 and bonded (e.g. using solder or another electrically conductive paste) to a respective bond pad 14a-14b, and a distal end 19a-19b extending downwardly from the proximal end. The plurality of leads 17a-17b may be L-shaped or T-shaped in some embodiments.

The gas sensor device 10 illustratively includes encapsulation material 20 filling the space between the proximal ends 18a-18b of the plurality of leads 17a-17b (i.e. electrically insulating the leads from each other) and the frame 15.

In particular, the frame 15, the encapsulation material 20, and the proximal ends 18a-18b of the plurality of leads 17a-17b are aligned to define an upper surface 22 of the gas sensor device 10. Also, the gas sensor device 10 illustratively includes additional encapsulation material 21 adjacent (and aligned with in the illustrated embodiment) the plurality of leads 17a-17b to define a sidewall 25 of the gas sensor device.

The frame 15 and the gas sensing surface 12 may be in spaced relation to define a gas sensing cavity 23 therebetween. The distal ends 19a-19b of the plurality of leads 17a-17b may extend past the backside surface 13 to define a recess 27. The purpose of recess 27 is to provide for IC die thickness variance and in case of over flow when dispensing an adhesive layer 24.

In the illustrated embodiment, the gas sensor device 10 further includes the adhesive layer 24 between the gas sensor IC 11 and the plurality of leads 17a-17b. The adhesive layer 24 provides a seal (e.g. hermetic) for the recess 27 when mounted. Also, the frame 15 is illustratively rectangle-shaped, and each gas passageway 16a-16d is illustratively cylinder-shaped. Other gas passageway 16a-16d shapes are possible, such as rectangle/square shapes. Also, the frame 15 may have other shapes. For example, the plurality of leads 17a-17b and the plurality of bond pads 14a-14b may each comprise at least one of copper and aluminum, and the encapsulation material 20-21 may comprise a dielectric material (e.g. molding compound). Also, in the illustrated embodiment, the plurality of leads 17a-17b provides a quad-flat no-leads (QFN) package for the gas sensor device 10.

Advantageously, the gas sensor device 10 may provide an approach to problems with the prior art gas sensor device 90. In particular, the prior art gas sensor device 90 has a large side profile and fails to meet height caps for many applications. Differently, the gas sensor device 10 has a thin low profile, which readily fits into a wide variety of gas sensing applications, and is also less costly to manufacture. Also, the gas passageways 16a-16d may be formed from high resolution and high precision etching processes, which provides improved performance over the wire mesh 95 of the prior art gas sensor device 90.

Referring now additionally to FIGS. 3A-7, a method of making one or more gas sensor devices 10a-10b. The method may include forming a frame 15a-15b having a plurality of gas passageways 16aa-16db extending therethrough, and forming a plurality of leads 17aa-17bb, each having a proximal end 18aa-18bb spaced from the frame, and a distal end 19aa-19bb extending downwardly from the proximal end. The method may include positioning a gas sensor IC 11a-11b having a gas sensing surface 12a-12b adjacent the plurality of gas passageways 16aa-16db, and a plurality of bond pads 14aa-14bb adjacent thereto and bonded to a respective proximal end 18aa-18bb. The method may further include forming encapsulation material 20a-21b to fill the space between the proximal ends 18aa-18bb of the plurality of leads 17aa-17bb and the frame 15a-15b.

Figure 3A:
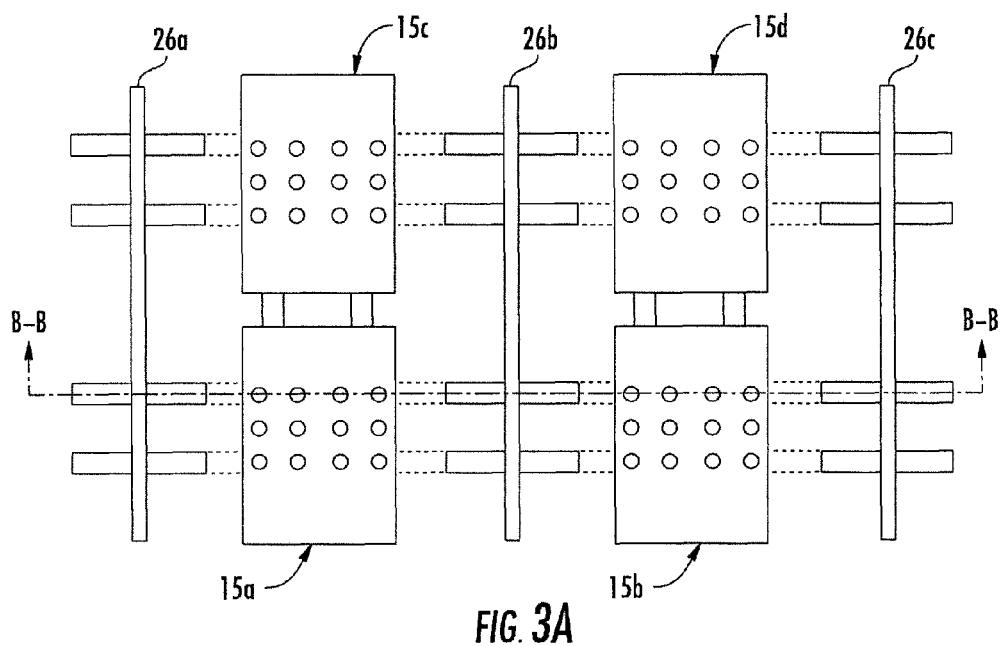
FIG. 3A is a schematic diagram of a top plan view of a step in making a gas sensor device, according to the present disclosure.
Figure 3B:
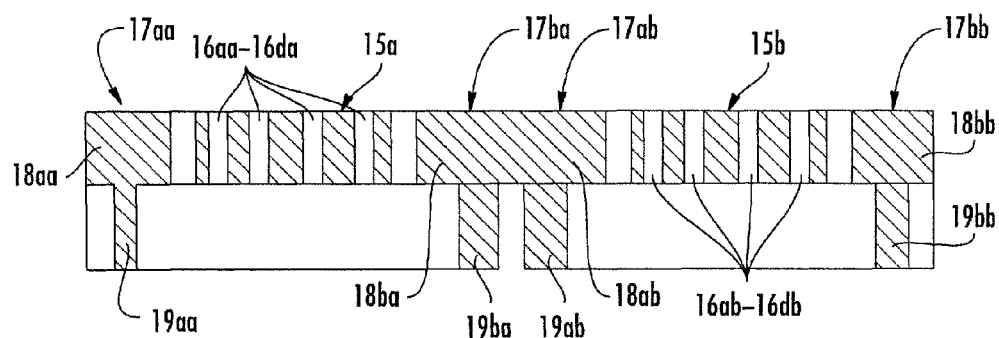
FIG. 3B is a schematic diagram of a cross-section view of the step in making the gas sensor device of FIG. 3A along line B-B.

Referring now particularly to FIGS. 3A and 3B, the method includes forming from a solid piece of electrically conductive material (e.g. copper, aluminum) the frames 15a-15d and three separate pieces 26a-26c, which will subsequently form the plurality of leads 17aa-17bb. Also, as noted with the dashed lines in FIG. 3A, the frames 15a-15d and three separate pieces 26a-26c may be coupled together to ease subsequent processing steps. The step may include a chemical etching and final singulation process. Advantageously, the etching process may afford a resolution superior to that of the wire mesh of the prior art approach.

Figure 4A:
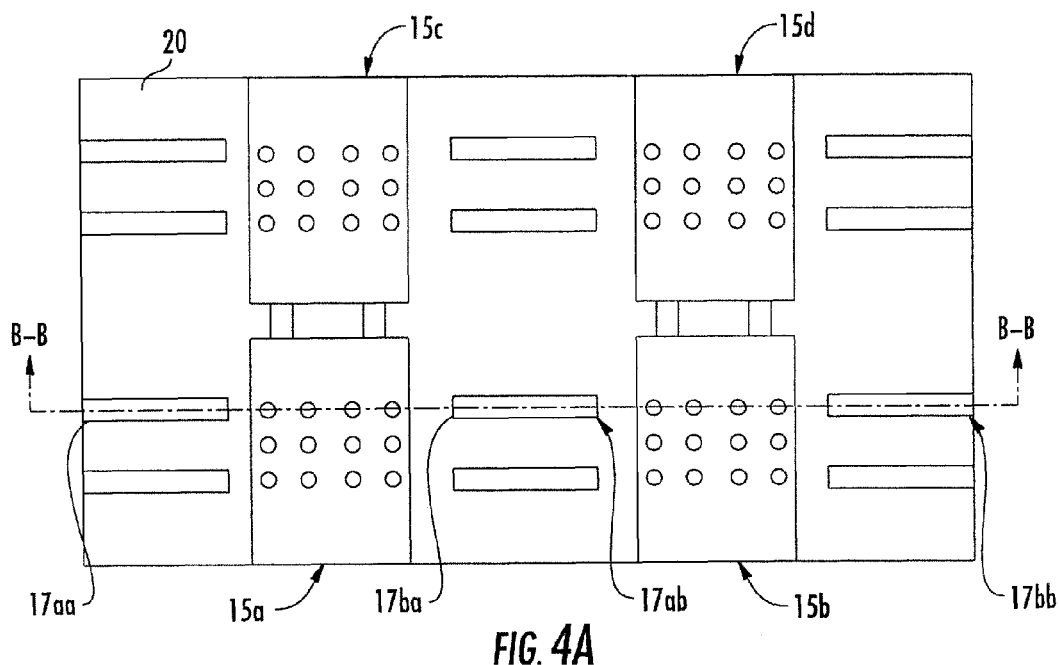
FIG. 4A is a schematic diagram of a top plan view of another step in making the gas sensor device, according to the present disclosure.
Figure 4B:
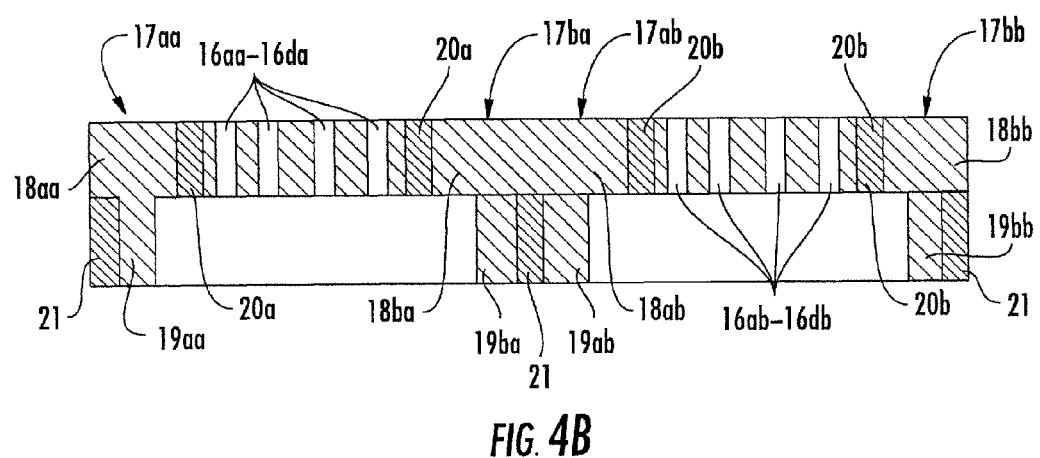
FIG. 4B is a schematic diagram of a cross-section view of the step in making the gas sensor device of FIG. 4A along line B-B.
Figure 5:
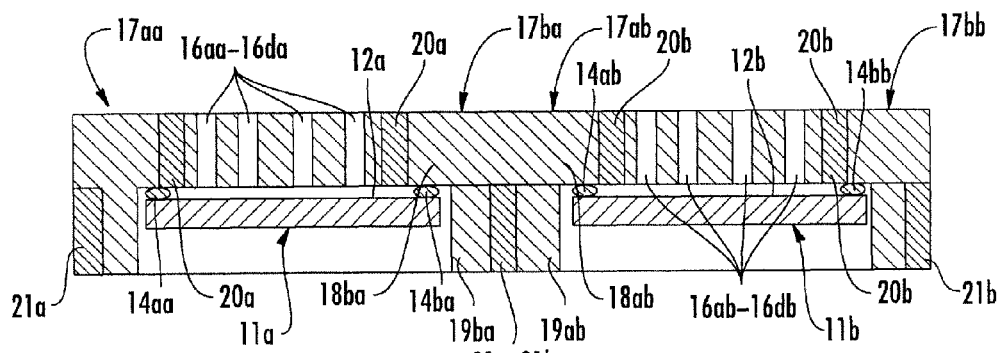
FIGS. 5-7 are schematic diagrams of cross-section views of additional steps in making the gas sensor device along line B-B.
Figure 6:
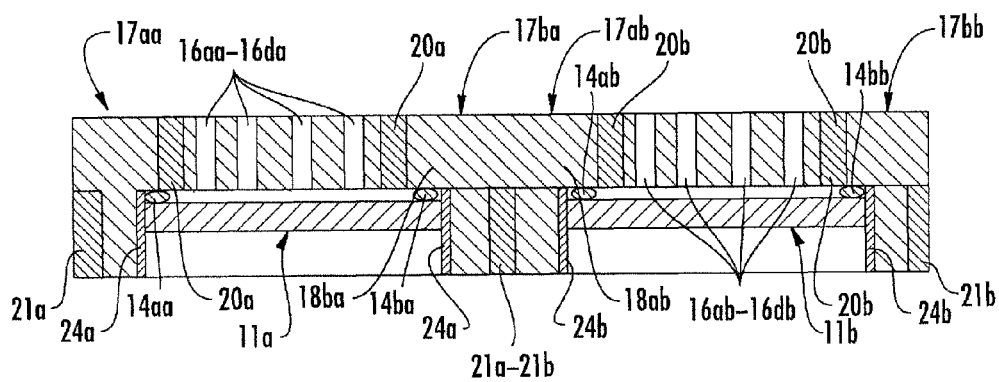
Figure 7:
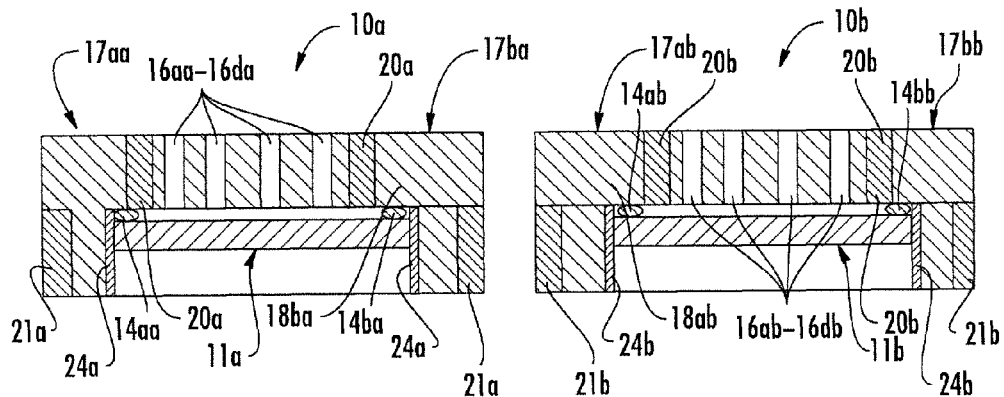

In FIGS. 4A-4B, the formation process from FIGS. 3A-3B is completed, and the encapsulation material 20a-21b is formed. In FIG. 5, the gas sensor ICs 11a-11b are mounted (flip-chip arrangement), and in FIG. 6, the adhesive layer 24a-24b is formed and cured between the plurality of leads 17aa-17bb and the gas sensor ICs. In FIG. 7, the gas sensor devices 10a-10b are singulated via a blade, for example. Although not depicted, it should be appreciated that a carrier layer could be used in the illustrated process, and that more devices could be made simultaneously with wafer level processing techniques.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

That which is claimed is:

1. A gas sensor device comprising:
   a gas sensor integrated circuit (IC) having a gas sensing surface, and a plurality of bond pads adjacent thereto;
   a frame having a plurality of gas passageways extending therethrough adjacent the gas sensing surface;
   a plurality of lead frame bodies, each lead frame body being devoid of a bond wire and having
      a proximal end spaced from said frame, said proximal end being over and bonded to a respective bond pad, and
      a distal end extending downwardly from the proximal end; and
   encapsulation material filling a space between the proximal ends of said plurality of lead frame bodies and said frame;
   said frame, said encapsulation material, and the proximal ends of said plurality of lead frame bodies being adjacent to define an upper surface of the gas sensor device;
   the proximal ends of said plurality of lead frame bodies being exposed at the upper surface of the gas sensor device.

2. The gas sensor device of claim 1 wherein said frame and the gas sensing surface are in spaced relation to define a gas sensing cavity therebetween.

3. The gas sensor device of claim 1 wherein said gas sensor IC has a backside surface opposite the gas sensing surface; and wherein the distal ends of said plurality of lead frame bodies extend past the backside surface to define a recess.

4. The gas sensor device of claim 1 further comprising an adhesive layer between said gas sensor IC and said plurality of lead frame bodies.

5. The gas sensor device of claim 1 further comprising additional encapsulation material adjacent said plurality of lead frame bodies to define a sidewall of the gas sensor device.

6. The gas sensor device of claim 1 wherein said frame is rectangle-shaped.

7. The gas sensor device of claim 1 wherein each gas passageway is cylinder-shaped.

8. The gas sensor device of claim 1 wherein said plurality of lead frame bodies and said plurality of bond pads each comprises at least one of copper and aluminum.

9. The gas sensor device of claim 1 wherein said encapsulation material comprises a dielectric material.

10. A gas sensor device comprising:
a gas sensor integrated circuit (IC) having a gas sensing surface, and a plurality of bond pads adjacent thereto;
a frame having a plurality of gas passageways extending therethrough adjacent the gas sensing surface, said frame and the gas sensing surface being in spaced relation to define a gas sensing cavity therebetween;
a plurality of lead frame bodies, each lead frame body being devoid of a bond wire and having
a proximal end spaced from said frame, said proximal end being over and bonded to a respective bond pad, and
a distal end extending downwardly from the proximal end;
an adhesive layer between said gas sensor IC and said plurality of lead frame bodies; and
encapsulation material filling a space between the proximal ends of said plurality of lead frame bodies and said frame;
said frame, said encapsulation material, and the proximal ends of said plurality of lead frame bodies being aligned to define an upper surface of the gas sensor device;
the proximal ends of said plurality of lead frame bodies being exposed at the upper surface of the gas sensor device.

11. The gas sensor device of claim 10 wherein said gas sensor IC has a backside surface opposite the gas sensing surface; and wherein the distal ends of said plurality of lead frame bodies extend past the backside surface to define a recess.

12. The gas sensor device of claim 10 further comprising additional encapsulation material adjacent said plurality of lead frame bodies to define a sidewall of the gas sensor device.

13. The gas sensor device of claim 10 wherein said frame is rectangle-shaped.

14. The gas sensor device of claim 10 wherein each gas passageway is cylinder-shaped.

15. A method of making a gas sensor device comprising:
forming a frame having a plurality of gas passageways extending therethrough, and forming a plurality of lead frame bodies, each lead frame body being devoid of a bond wire and having
a proximal end spaced from the frame, and
a distal end extending downwardly from the proximal end;
positioning a gas sensor integrated circuit (IC) having a gas sensing surface adjacent the plurality of gas passageways, and a plurality of bond pads adjacent thereto and bonded to a respective proximal end, the respective proximal end being over a respective bond pad; and
forming encapsulation material to fill a space between the proximal ends of the plurality of lead frame bodies and the frame;
said frame, the encapsulation material, and the proximal ends of the plurality of lead frame bodies being adjacent to define an upper surface of the gas sensor device;
the proximal ends of the plurality of lead frame bodies being exposed at the upper surface of the gas sensor device.

16. The method of claim 15 wherein the frame and the gas sensing surface are in spaced relation to define a gas sensing cavity therebetween.

17. The method of claim 15 wherein the gas sensor IC has a backside surface opposite the gas sensing surface; and wherein the distal ends of the plurality of lead frame bodies extend past the backside surface to define a recess.

18. The method of claim 15 further comprising forming an adhesive layer between the gas sensor IC and the plurality of lead frame bodies.

19. The method of claim 15 further comprising forming additional encapsulation material adjacent the plurality of lead frame bodies to define a sidewall of the gas sensor device.

20. The method of claim 15 wherein the frame is rectangle-shaped.

21. The method of claim 15 wherein each gas passageway is cylinder-shaped.

22. The method of claim 15 wherein the plurality of lead frame bodies and the plurality of bond pads each comprises at least one of copper and aluminum.

23. The method of claim 15 wherein the encapsulation material comprises a dielectric material.

* * * * *